United States Patent [19]

Sasso et al.

[11] Patent Number: 5,643,259

[45] Date of Patent: Jul. 1, 1997

[54] SPINE FIXATION INSTRUMENTATION

[75] Inventors: Ricardo C. Sasso, 9436 Spring Mill Dr., Indianapolis, Ind. 46260; Daniel F. Justin, Orlando, Fla.

[73] Assignee: Ricardo C. Sasso, Indianapolis, Ind.

[21] Appl. No.: 220,736

[22] Filed: Mar. 31, 1994

[51] Int. Cl.⁶ .................................................. A61B 17/56
[52] U.S. Cl. .................................................. 606/61
[58] Field of Search ................................ 606/61, 60, 73; 403/374, 373

[56] References Cited

U.S. PATENT DOCUMENTS 5,053,034  10/1991  Olerod ...................... 606/61
5,218,222  6/1993   Allard et al. .
5,306,275  4/1994   Brgan ....................... 606/61

*Primary Examiner*—Michael Powell Buiz
*Assistant Examiner*—Mark S. Leonardo
*Attorney, Agent, or Firm*—Woodard, Emhardt, Naughton, Moriarty & McNett

[57] ABSTRACT

Spine fixation instrumentation including a rod and lateral mass screws which can be fixed at any of a range of orientations relative to the rod. Connectors are used to couple the rod and the screws. Sleeves are wedged between yokes on the one hand and the rod or shafts on the other hand. The sleeves are assembled and disassembled by instruments similar to pliers.

8 Claims, 6 Drawing Sheets

SPINE FIXATION INSTRUMENTATION

This invention relates to spine fixation instrumentation finding particular utility in the setting of the cervical spine.

BACKGROUND OF THE INVENTION

When placing lateral mass screws in the cervical spine it is desirable in certain situations to have the screw project into the bone upwardly and outwardly at an angle of approximately 30 degrees upward and 30 degrees outward. It is difficult to achieve such orientation with existing instrumentation without bending of the rod making up a part of the instrumentation. Presently available instrumentation does not permit optional screw placement and does not permit independent screw placement. Further, after presently available instrumentation has served its purpose and it is time for it's disassembly from the patient, disassembly is frequently difficult and time consuming. Still another problem with existing instrumentation is that it is relatively difficult to assemble and install. Further, there is not presently available for the cervical spine a system for fixing lateral mass screws to a rod. This invention is intended to address these problems.

The following references disclose instrumentation for fixation of the spine: U.S. Pat. No. 4,662,365 Gotzen et al.; U.S. Pat. No. 4,887,596 Sherman; U.S. Pat. No. 4,957,495 Kluger; and U.S. Pat. No. 5,254,118 Mirkovic. The following references disclose instrumentation for correcting various spinal deformities and related matters: U.S. Pat. No. 4,433,676 to Babechko; U.S. Pat. No. 4,773,402 to Asher et al.; U.S. Pat. No. 4,815,453 to Cotrel; U.S. Pat. No. 5,010,879 to Moriya et al.; U.S. Pat. No. 5,092,866 to Bread et al.; U.S. Pat. No. 5,147,359 to Cozad et al.; U.S. Pat. No. 5,147,360 to Dubousset; U.S. Pat. No. 5,154,718 to Cozad et al.; 5,181,917 to Rogozinski; 5,201,734 to Cozad et al.; 5,217,497 to Mehdian; 5,281,222 to Allard et al. and European patent application 0 452 792 A1.

SUMMARY OF THE INVENTION

One embodiment of the present invention might involve a spine fixation instrumentation including a screw threaded at one end for insertion into the bone and having a first yoke at the other end. There is also provided a rod adapted to be arranged parallel to the spine. A first connector is used to fixedly connect the screw to the rod. The first connector includes a second yoke and a first shaft mounted on the second yoke. A first tapered sleeve is received on the shaft and is wedged between the first yoke and the shaft and fixes the screw to the connector. A second tapered sleeve is received on the rod and is wedged between the second yoke and the rod and fixes the connector to the rod.

Another embodiment of the present invention might involve a method for fixation of the spine including providing a first screw threaded at one end and having a first yoke at the other end. The first screw is screwed into the bone at a desired attitude and location. A rod is arranged parallel to the spine. A first connector is provided which has a second yoke and a first shaft mounted on said second yoke. The method further includes the steps of wedging a first tapered sleeve on said shaft and between said shaft and said first yoke, and wedging a second tapered sleeve on said rod and between said rod and said second yoke.

DESCRIPTION OF THE PREFERRED EMBODIMENT

Figure 1:
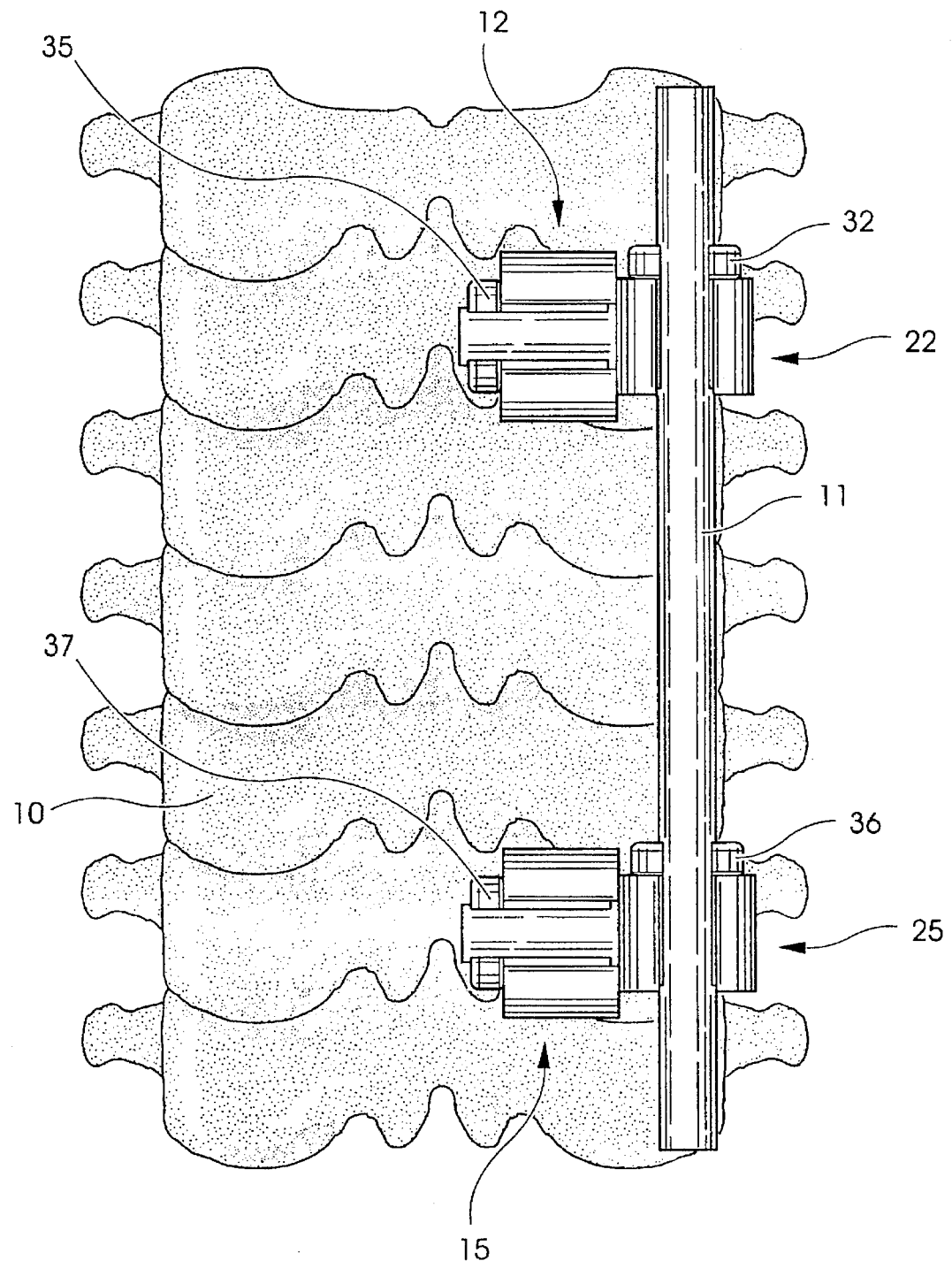
FIG. 1 is a rear elevational view of the cervical spine showing the installed instrumentation of this invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
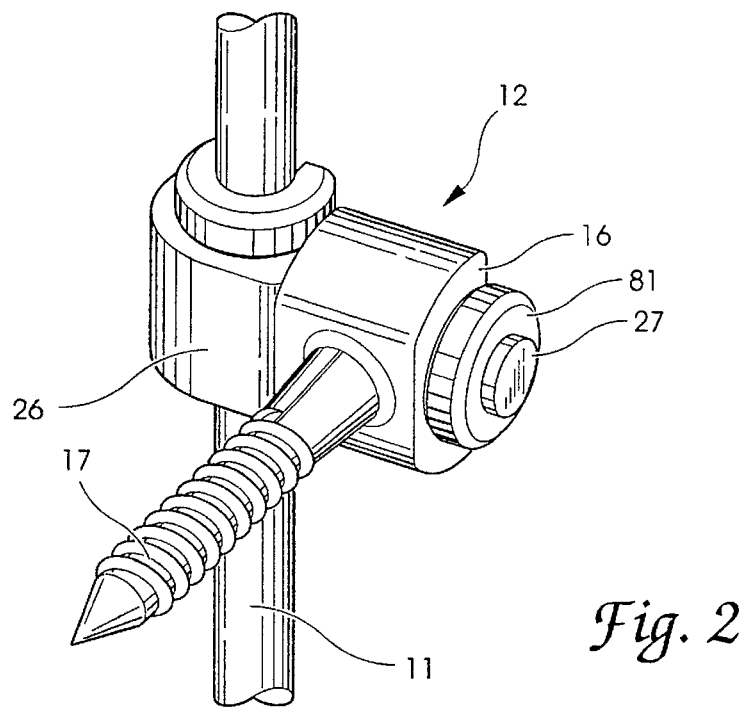
FIG. 2 is a perspective view of a portion of the structure illustrated in FIG. 1.
Figure 3:
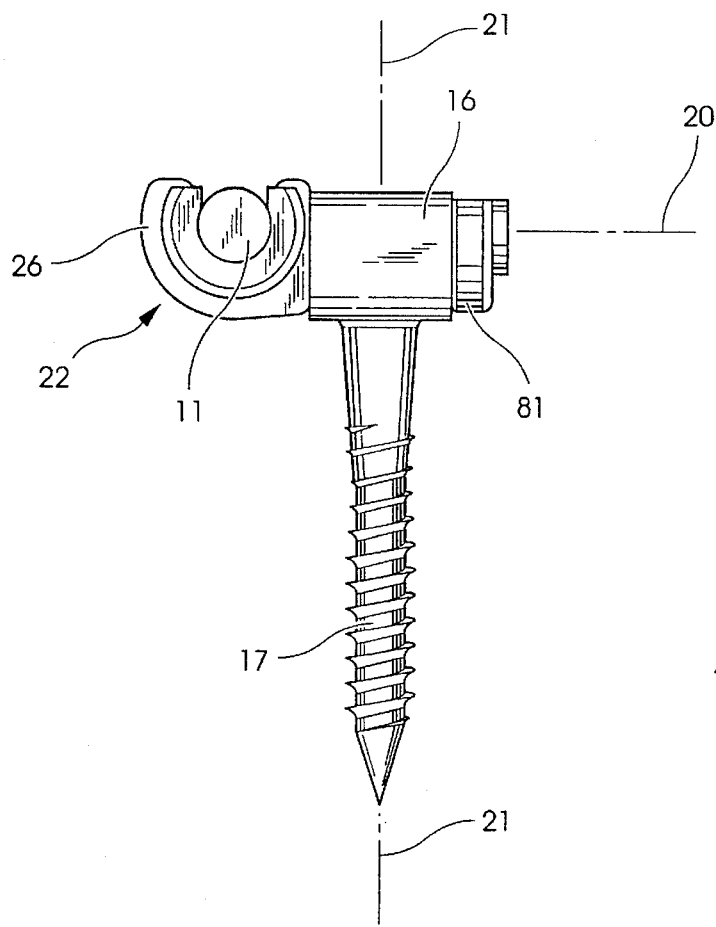
FIG. 3 is a side elevational view of the structure of FIG. 2.
Figure 4:
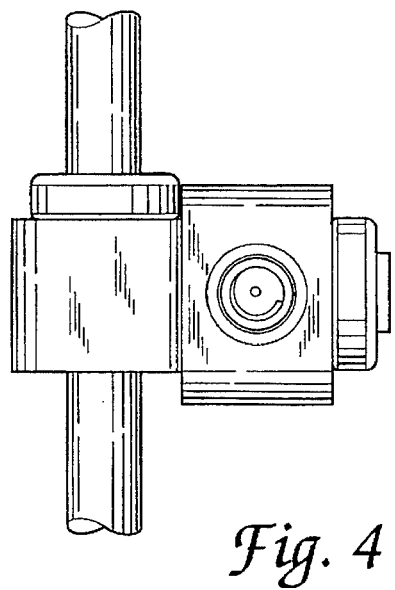
FIG. 4 is a front elevational view of the structure of FIG. 2 and FIG. 3.
Figure 5:
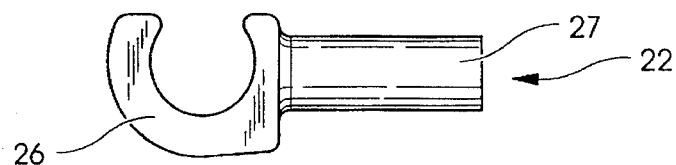
FIG. 5 is a side elevation of a connector making up a part of the instrumentation.
Figure 6:
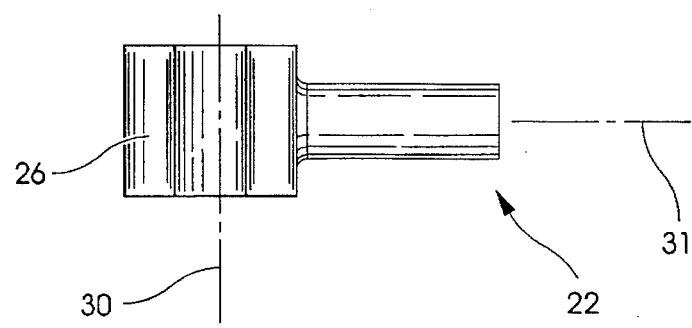
FIG. 6 is a further side elevation of the connector taken at 90 degrees to FIG. 5.

Referring to FIG. 1 there is shown a rear elevation of the cervical spine 10. The spinal fixation instrumentation installed therein includes a rod 11 extending generally parallel to the spine and lateral mass screws 12 and 15 which are threaded into the bone. A representative one 12 of the lateral mass screws (which are identical) is shown in FIG. 2 as including a yoke 16 and a threaded portion 17. The yoke 16 and the threaded portion 17 each have axes 20 and 21 which are perpendicular to one another.

The rod 11 is coupled to the screw 12 by connector 22. Similarly the screw 15 is coupled to the rod 11 by a connector 25. The connectors 22 and 25 are identical and connector 22 is described below as representative of the connector 25 as well. The connector 22 includes a yoke 26 and a shaft 27 integral with the yoke 26. The yoke 26 and shaft 27 have respectively axes 30 and 31 which are perpendicular to one another.

Figure 7:
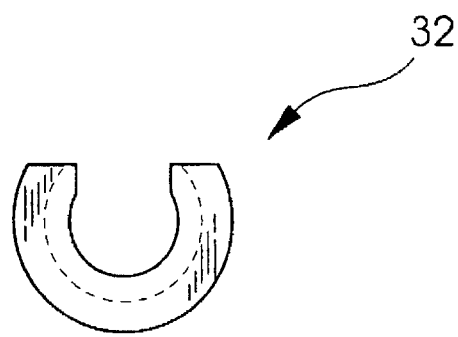
FIG. 7 is an end elevation of a sleeve making up a part of the instrumentation.
Figure 8:
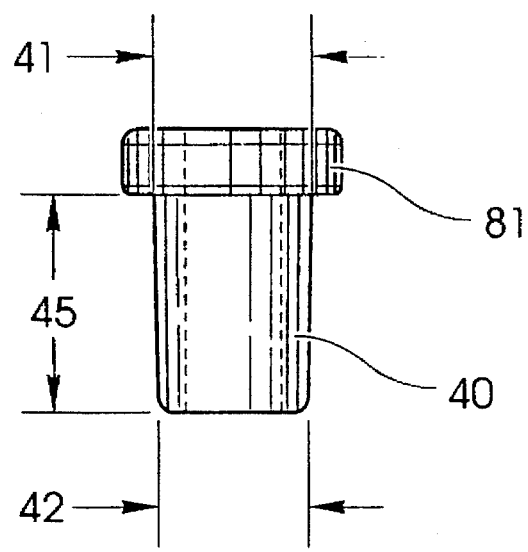
FIG. 8 is a side elevation of the sleeve of FIG. 7.

The structure illustrated in FIG. 1 is fixed together by sleeves 32, 35, 36 and 37 all of which are identical. A representative one of the sleeves is shown in FIG. 7 and FIG. 8. The external surface 40 of the sleeve 32 is generally cylindrical but is also tapered. Thus in one representative example of the invention the sleeve 32 tapers from 0.208 in.±0.001 at 41 to 0.198 in.±0.001 at 42. The lengthwise distance 45 of the sleeve in the tapered area is 0.276 inches.

In order to couple the various parts of the instrumentation together the sleeves 32, 35 36 and 37 are driven into respective yokes 26, 16, 26 and 16. Each of the yokes have an internal part cylindrical configuration which in the representative sample of the invention had an internal diameter of 0.206 in.±0.002. When the sleeve 32, 35, 36 and 37 is driven into the yoke it also is caused to tightly grip the rod 11 or shaft 27. The external dimension or outside diameter of the rod 11 and shafts 27 is in the representative example equal to 0.138 inches.

It can been seen that the present instrumentation makes possible orienting the lateral mass screws at a range of distances from the rod and at any desired angle or attitude.

Figure 9:
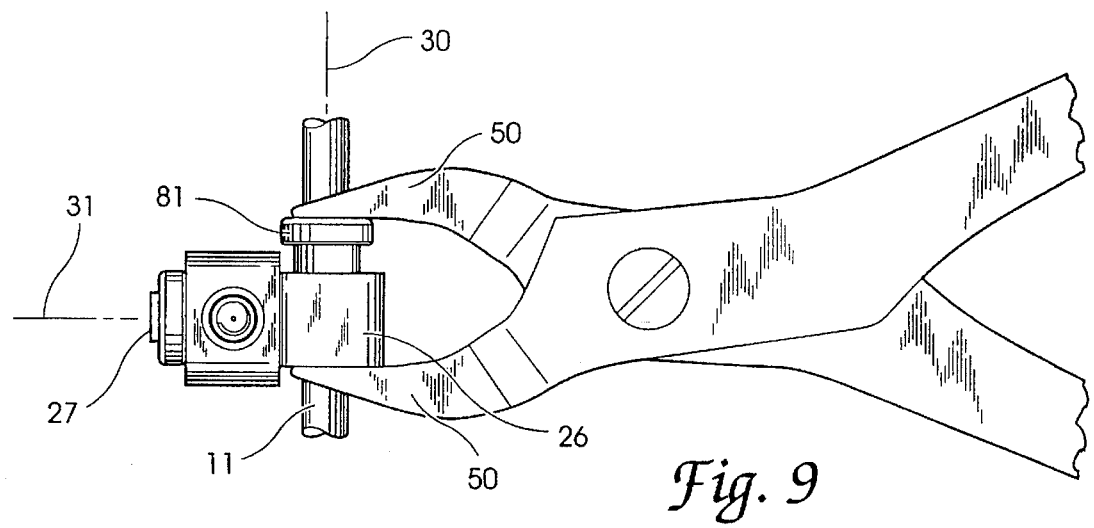
FIG. 9 is a view taken at 90 degrees to the view of FIG. 3 and also showing an installation tool.
Figure 9A:
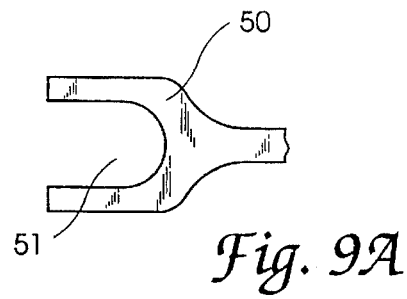
FIG. 9A is a fragmentary view taken at 90 degrees to the view of FIG. 9 showing the jaw of the tool.

Referring to FIG. 9 there is illustrated a tool for forcing the sleeves 23, 25, 26 and 37 into the respective yokes. The tool is similar to a pair of pliers in that it has jaws so as to engage the respective sleeves and yokes to force the sleeves into the yokes and to wedge the sleeve between the yoke and the rod or shaft. The jaws 50 are shaped so as to provide a slot 51 which surrounds the rod or shaft so that the jaws can properly seat against the sleeve and yoke to force the sleeve into the yoke.

Figure 10:
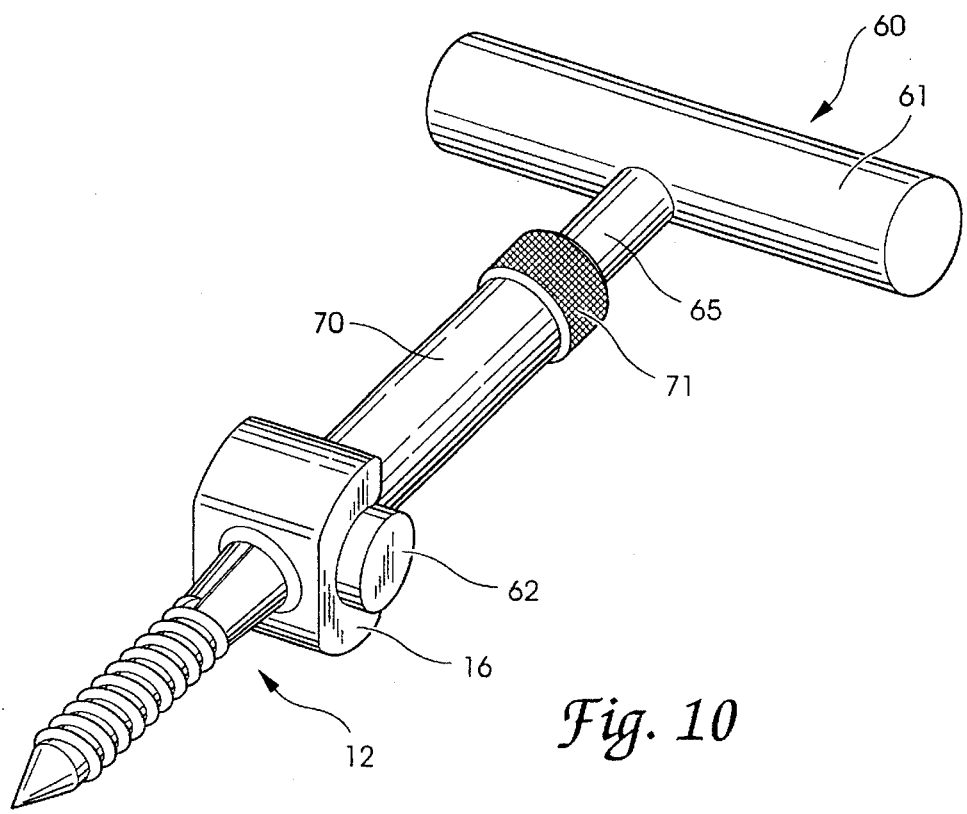
FIG. 10 is a perspective view of still another installation tool showing it coupled to a lateral mass screw of the present invention.
Figure 11:
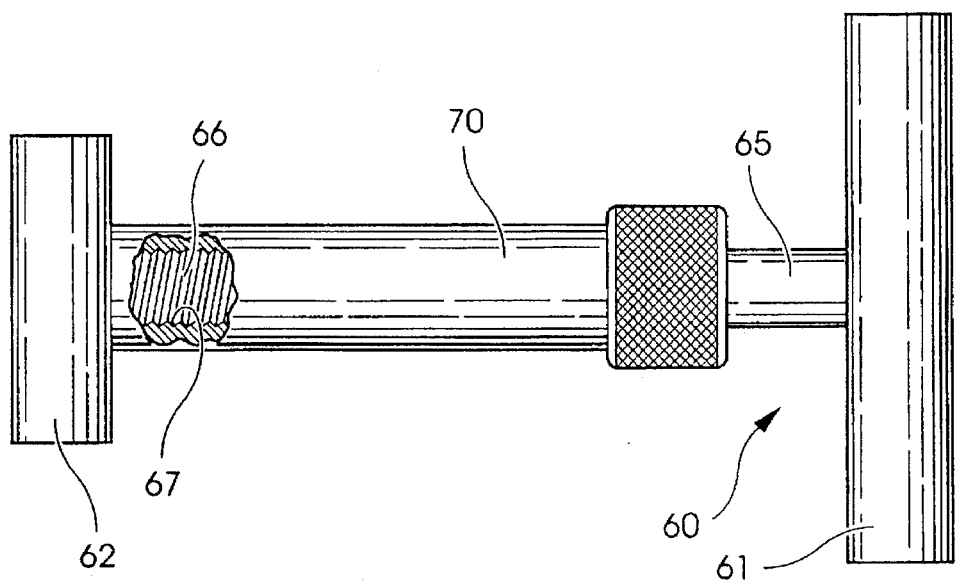
FIG. 11 is a side elevational view of the tool of FIG. 10.

FIGS. 10 and 11 show a tool 60 for driving in the lateral mass screw 12. The tool includes a handle 61 and a cylindrical section 62 coupled to the handle by a member 65. The member 65 has threads 66 which are engaged by internal threads 67 in a sleeve 70. The sleeve 70 has knurling 71 which assists in rotating the sleeve to bear down against the yoke 16 on the lateral mass screw. The tool is used to screw in and take out the lateral mass screws. The sleeve 70 makes possible the tool being secured to the pedicle screw in a firm and rigid fashion for installing and taking out the lateral mass screws.

One embodiment of the method of fixation of the spine of this invention includes the steps of driving the screw 12 into the bone at a desired attitude and location. The screw may be placed, for example, in an up and out position typical of a lateral mass screw placement with the yoke 16 located medially of the screw threads. The tool 60 may be used to effect such placement of the screw 12. A further screw 15 is also driven into the bone at a desired attitude and location. The rod 12 is arranged parallel to the spine. The screws 12 and 15 are fixed relative to the rod by connectors 22 and 25. The entire assembly is fixed together by wedging the sleeves 23, 25, 26 and 37 into the respective yokes 26, 16, 26 and 16. This invention also has application in the situation that the screws function as thoracic pedicle screws, occipital screws and/or transarticular screws.

Figure 12:
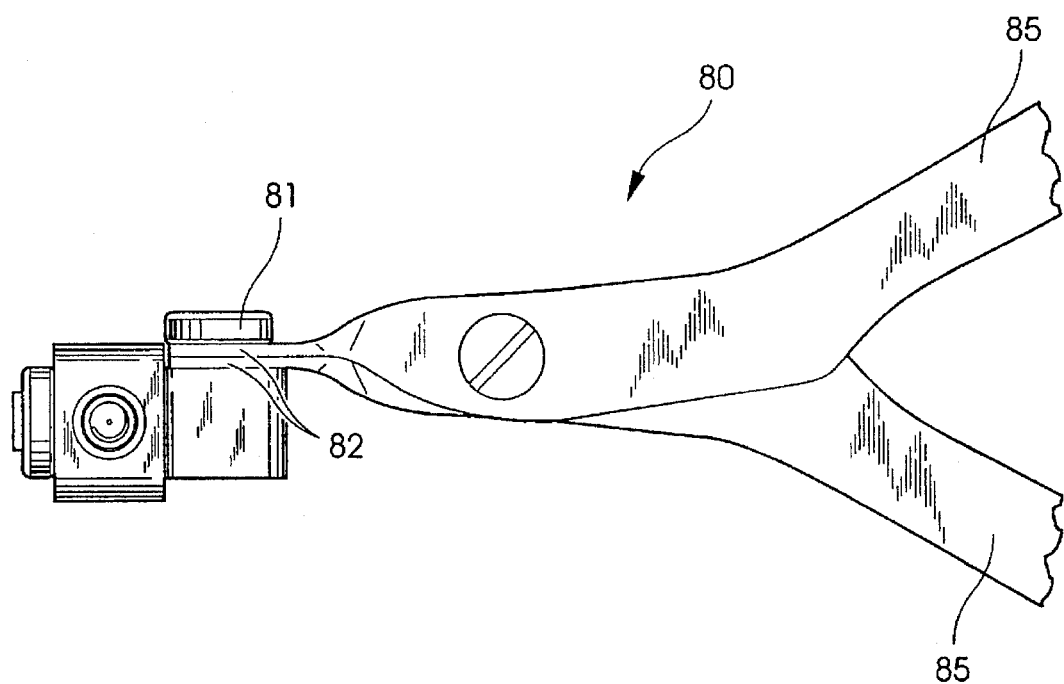
FIG. 12 is a side elevational view of a tool for disassembly of the instrumentation.

In order to disassemble the instrumentation the sleeves are removed from the yokes. This can be accomplished by a small screw driver or by the tool 80 shown in FIG. 12. Each of the sleeves 32, 35, 36 and 37 has a collar 81. The tool 80 has fingers 82 that are forced apart by the forcing together of the handles 85 causing the sleeves to be forced out of the respective yokes. In the event a small screw driver is used to pry loose the wedging sleeve, it is wedged and toggled between the collar on the sleeve and the yoke.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. Spine fixation instrumentation comprising:

a first screw threaded at one end for insertion into bone and having a first yoke at the other end;

a rod adapted to be arranged parallel to the spine;

a first connector for fixedly connecting the screw to the rod including a second yoke and a first shaft fixedly mounted on said second yoke;

a first tapered sleeve received on said first shaft and wedged between said first yoke and said first shaft and fixing said first screw to said first connector; and a second tapered sleeve received on said rod and wedged between said second yoke and said rod and fixing said first connector to said rod.

2. The spine fixation instrumentation of claim 1 additionally comprising:

a second screw threaded at one end for insertion into the bone and having a third yoke at the other end;

a second connector for fixedly connecting the second screw to the rod including a fourth yoke and a second shaft fixedly mounted on said fourth yoke;

a third tapered sleeve received on said second shaft and wedged between said third yoke and said second shaft and fixing said second screw to said second connector; and a fourth tapered sleeve received on said rod and wedged between said fourth yoke and said rod and fixing said second connector to said rod.

3. The spine fixation instrumentation of claim 1 wherein said first screw has threads oriented about a first axis, said first yoke has a second axis and said first and second axes are perpendicular to one another.

4. The spine fixation instrumentation of claim 3 wherein said second yoke has a third axis, said first shaft has a fourth axis and said third and fourth axes are perpendicular to one another.

5. The spine fixation instrumentation of claim 2 wherein said first screw has threads oriented about a first axis; said first yoke has a second axis; said first and second axes are perpendicular to one another; said second yoke has a third axis; said first shaft has a fourth axis; said third and fourth axes are perpendicular to one another; said second screw has threads oriented about a fifth axis, said third yoke has a sixth axis, said fifth and sixth axes are perpendicular to one another, said fourth yoke has a seventh axis, said second shaft has an eighth axis and said seventh and eighth axes are perpendicular to one another.

6. The spine fixation instrumentation of claim 1 wherein said sleeves are identical, each of said sleeves being split and having a C-shaped cross section.

7. The spine fixation instrumentation of claim 5 wherein said sleeves are identical, each of said sleeves being split and having a C-shaped cross section.

8. The spine fixation instrumentation of claim 7 wherein each of said sleeves has a collar, said sleeves being removable from the yoke into which they are wedged by inserting a tool between the collar and the yoke.

* * * * *